United States Patent
Dacquin et al.

(10) Patent No.: US 10,282,832 B2
(45) Date of Patent: May 7, 2019

(54) METHOD AND INSTALLATION FOR IMAGING A FRAGMENTATION PATTERN FORMED IN A TEMPERED GLASS PANEL

(71) Applicant: AGC GLASS EUROPE, Louvain-la-Neuve (BE)

(72) Inventors: Romain Dacquin, Basecles (BE); Nerio Lucca, Fleurus (BE)

(73) Assignee: AGC GLASS EUROPE, Louvain-la-Neuve (BE)

( * ) Notice: Subject to any disclaimer, the term of this patent is extended or adjusted under 35 U.S.C. 154(b) by 0 days.

(21) Appl. No.: 15/328,251

(22) PCT Filed: Jul. 15, 2015

(86) PCT No.: PCT/EP2015/066123
§ 371 (c)(1),
(2) Date: Jan. 23, 2017

(87) PCT Pub. No.: WO2016/012321
PCT Pub. Date: Jan. 28, 2016

(65) Prior Publication Data
US 2017/0221198 A1    Aug. 3, 2017

(30) Foreign Application Priority Data

Jul. 24, 2014  (EP) .................................... 14178286

(51) Int. Cl.
| | | |
|---|---|---|
| *G06K 9/00* | (2006.01) | |
| *G06T 7/00* | (2017.01) | |
| *G01N 33/38* | (2006.01) | |
| *G01N 21/88* | (2006.01) | |
| *G01N 21/958* | (2006.01) | |

(52) U.S. Cl.
CPC ....... *G06T 7/0006* (2013.01); *G01N 21/8806* (2013.01); *G01N 21/958* (2013.01); *G01N 33/386* (2013.01); *G01N 2021/9586* (2013.01)

(58) Field of Classification Search
None
See application file for complete search history.

(56) References Cited

U.S. PATENT DOCUMENTS

| 5,128,550 A * | 7/1992 | Erbeck ................. G01N 21/958 |
| | | 250/559.01 |
| 2010/0007887 A1* | 1/2010 | Aldred ................... G01N 3/307 |
| | | 356/432 |
| 2012/0098959 A1 | 4/2012 | Addington | |

OTHER PUBLICATIONS

International Search Report dated Jan. 5, 2016, in PCT/EP2015/066123, filed Jul. 15, 2015.

(Continued)

*Primary Examiner* — Hadi Akhavannik
(74) *Attorney, Agent, or Firm* — Oblon, McClelland, Maier & Neustadt, L.L.P.

(57) ABSTRACT

A method and installation of inspecting a fragmentation pattern of a tempered glass panel by deflectometry, following a fragmentation test, the method including: (i) positioning the tempered glass panel in contact with a support; (ii) projecting by a display device a structured light pattern on the surface of at least one portion of the tempered glass panel; (iii) capturing an image reflected by the surface of the first portion of the tempered glass panel using an image capture device; and (vi) processing the images to determine the fragmentation pattern by an image processing device.

15 Claims, 1 Drawing Sheet

(56) References Cited

OTHER PUBLICATIONS

Park et al., "A Two Dimensional Phase-Shifting Method for Deflectometry", Proceedings of SPIE—The International Society for Optical Engineering, vol. 7266, Nov. 2008, XP040446262, 11 pages.
Gordon, "Automated Glass Fragmentation Analysis", Proceedings of the SPIE, Machine Vision Applications in Industrial Inspection IV, vol. 2665, Feb. 1996, XP001011597, 9 pages.

\* cited by examiner

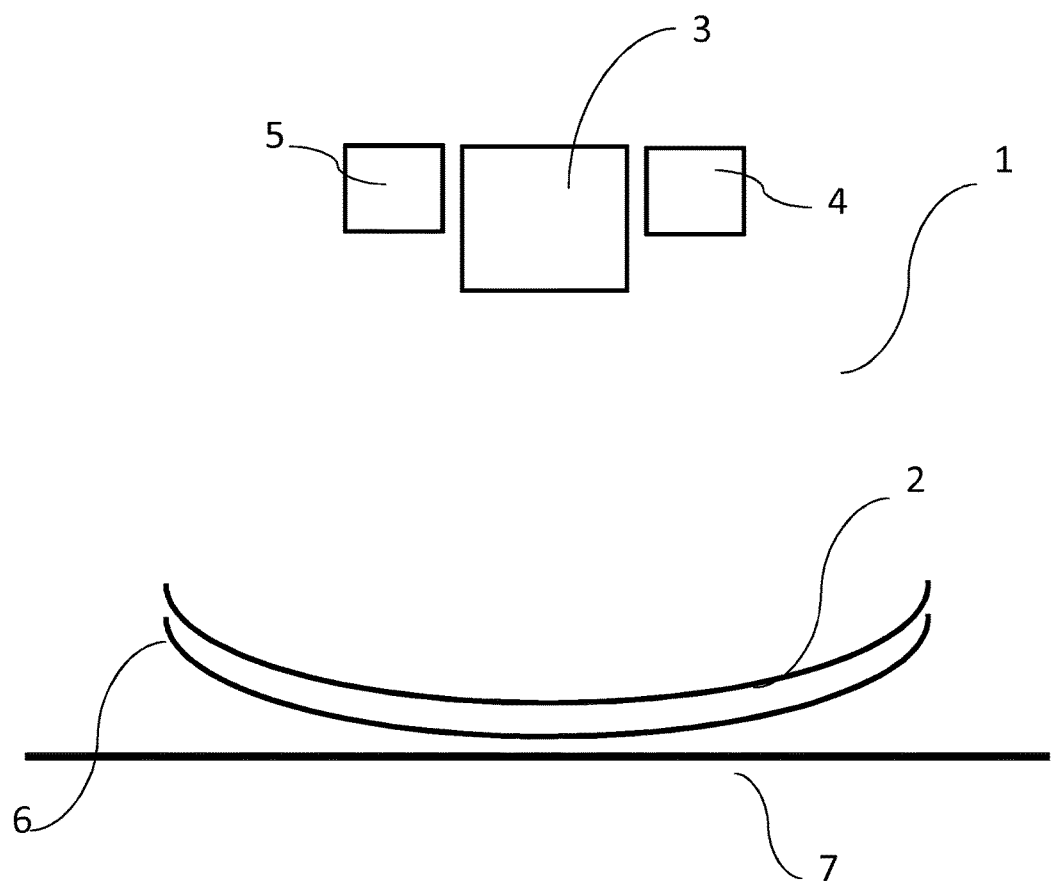

METHOD AND INSTALLATION FOR IMAGING A FRAGMENTATION PATTERN FORMED IN A TEMPERED GLASS PANEL

TECHNICAL DOMAIN OF THE INVENTION

The present invention relates to a method of and an installation for inspecting glazings, in particular, a method of imaging fragmentation patterns produced in a tempered glass panel.

BACKGROUND OF THE INVENTION

Optical inspections methods may be used to determine whether a glazing meets various safety standards. Typically, optical inspection methods are used to determine whether a glazing meets optical standards. However, optical inspection methods may also be used to help determine whether a glazing meets impact resistance standards.

Most of windowpanes for automotive and some glass panel for architectural use are made of tempered glass, which has held compressive stress applied to surfaces thereof to improve resistance to tensile stress. Tempering puts the outer surfaces into compression and the inner surfaces into tension. Such stresses cause the glass, when broken, to crumble into small granular chunks instead of splintering into jagged shards as plate glass create. The granular chunks are less likely to cause injury. As a result of its safety and strength, tempered glass is used in a variety of demanding applications, including windows, shower doors, architectural glass doors and tables, refrigerator trays, as a component of bulletproof glass, for diving masks, and various types of plates and cookware.

In the production of such a kind of glass, a fragmentation test is carried out as a quality assurance test.

Particularly, respectively for automotive use and architectural use, the fragmentation test for tempered glass are prescribed by ECE R43 and EN12150 standards which are the relevant safety standard in Europe.

The fragmentation test for tempered glass is a test wherein test glass is fragmented by applying an impact shock to a certain portion thereof with a punch, the number of fragments in a region with coarsest fragment included and in a region with the finest fragment included are calculated, and the area of the greatest fragment and the length of the longest fragment in that region are measured to see whether test glass meets desired specifications, or not.

For the calculation of the fragments or another purpose, a measuring method has been adopted wherein the image of fragmented test glass is exposed on photosensitive paper to obtain an image as a blueprint (herein below, referred to as a blueprinted image), and the measurement is conducted utilizing the blueprinted image. In the measuring method, all operations including the setting of selected regions and the calculation of the number of the fragments have been manually carried out based on the blueprinted image. The conventional measuring method has required considerable labor in the calculating operation for counting the number of the fragments and another operation.

As an example of systems to improve the reproducibility of the fragmentation test, "Automated calculating system for the ECE fragmentation test" of Ford Motor Co. (GLASS PROCESSING DAYS, 13-15 Sep. 1997) discloses a technique of the calculating operation for counting the number of the fragments and another operation in the blueprinted image are automatically carried out by a computer. According to this automated calculating technique, there is no need for an operator to manually count the number of the fragments, reducing the number of the steps required for the calculating operation.

Since the measurement of the number of the fragments and another operation have been manually made by an operator in the conventional manual measuring method for the fragmentation test the conventional manual measuring method has created some difficulties in that the calculating operation in the fragmentation test requires many steps and much labor cost.

An alternative method of imaging and processing the test data is disclosed in U.S. Pat. No. 6,766,046. A light source is positioned above a ply of glass supported on a paper screen held on a transparent guide sheet. A camera having a line sensor is positioned underneath the screen, to detect the image of the fragments projected onto the screen by the light source. Either the glass or the camera may be moved to ensure that the entire area of the ply of glass is scanned. The light source may be a point source, combined with a condensing lens, or an array of light sources.

The automation of the data collection and image processing reduces the time necessary to determine whether a ply of glass has passed or failed the fragmentation test. However, the use of the screen (where the camera records the screen image rather than a direct image from the glass) causes difficulties when glass having a low light transmission is tested. In U.S. Pat. No. 6,766,046, low light transmission is overcome by employing a photosensor to determine the light transmission of the glass so that the exposure time needed by the camera to record the image on the screen may be adjusted accordingly. However, for low light transmission glass, this increases the time required for data acquisition. For an automated system to be viable in a production situation, the image capture ideally needs to be completed within a three minutes time for a window.

There is therefore a need for an optical inspection system allows testing and measurement for the fragmentation test under, for example, ECE R43 for automotive glazing or EN12150 for architectural glazing to be carried out within a short time-frame, for both high and low light transmission glasses.

SUMMARY OF THE INVENTION

Accordingly, the present invention aims to address these problems by providing a method of inspecting a fragmentation pattern of a tempered glass panel, following a fragmentation test, the method comprising:
  positioning the tempered glass panel in contact with a support means;
  projecting thanks to a display device a structured light pattern on the surface of at least one portion of the tempered glass panel,
  capturing an image reflected by the surface of the first portion of the tempered glass panel using an image capture device, and
  processing the images to determine the fragmentation pattern thanks to an image processing device.

Pursuant to a further aspect of the present invention, the tempered glass panel tested is a glass panel for automotive use. The fragmentation test is then preferably carried out in accordance with ECE R43 standard.

In another embodiment of the present invention, the tempered glass tested is a glass panel for architectural use. Then, the fragmentation test is preferably carried out in accordance with EN12150 standard.

By providing a structured light pattern on the at least one portion of the surface of a tempered glass panel, the distorted image obtained by reflection of the structured light pattern by the said surface, a high resolution image of the fragmentation pattern can be obtained on even low light transmission glasses.

One of the advantages of the present invention is that privacy or tinted glass with a low light transmission coefficient could be analysed since the present invention is not sensitive to the colour or the light transmission of the glass. Thus, the present invention allows to acquire a good quality picture for privacy or tinted glass. The image can be more easily processed and more details like length of the longer fragment or the smallest fragment are obtained leading to a better understanding of the fragmentation pattern. The present invention is advantageous since it is not sensitive to the light transmission of glass. Thus, the quality of results is improved since the presence of folds resultant of plastic foil applied on the surface of the tested glass panel, does not impact the quality of image as for the current method used for the fragmentation test. Indeed, with the current method used for the fragmentation test, particularly in automotive field, the folds can be wrongly considered as crack.

According to the invention, all cracks resultant from the impact shock under the fragmentation test appear with the same light intensity. Thus, there is no doubt about the presence or not of a crack since cracks are easily identifiable (with a same light intensity) on the surface of tested glass panel and images with good quality are obtained.

Besides providing a method of inspecting a fragmentation pattern, the present invention allows to provide information leading to help to adapt conditions (time, temperature . . . ) of the furnace used for tempering the glass panel.

Accordingly to the invention, the projection of a structured light pattern on a surface of at least one portion of the surface of a glass panel and capturing the corresponding distorted image reflected from the said surface is based on the deflectometry principle meaning an optical contactless solution for the control of safety standards under ECE R43 for automotive glass or under EN12150 for architectural glass.

The inventors showed that surprisingly, with a deflectometry method, the method and consequently the analysis of images from the inspecting of a fragmentation pattern is improved. Thus, this invention allows to efficiently acquire a good quality picture even if the tested glass is a privacy or tinted glass since the present invention is not sensitive to the color of glass and particularly to the light transmission.

Finally, according to the present invention, the data are processed by automation. The automation of the data collection and particularly the quality of images captured and processed are improved. By directly picking up the test glass according to this method, a clear image can be provided, and operations, such as calculating the number of fragments for example in a specific area, can be automatically performed based on the image signals, allowing a fragmentation test to be carried out with good reproducibility and high precision.

Accordingly to the present invention, the structured light pattern projected on the surface of at least one portion of the tempered glass panel represents preferably fringes and images from the reflection from the surface wherein the structured light is projected are processed using the phase measuring deflectometry.

For example, the Visuol® technology, particularly as described in the patent application EP2386848, based on the optic principle of the deflectometry can be used. By replacing the eye with a high resolution camera, the goal of the measurement technique is to quantify the distortion of a structured light reflected onto the inspected surface. A structured light represented by periodic fringes is displayed on a screen, not projected onto the surface as in classical vision measuring system.

Fringes are understood to be a series of alternately light and dark and generally straight bands generated by the display device, which may be black and white or of any other color. A high resolution camera observes the reflected light onto the measured surface.

According to one embodiment of the present invention, the images are processed using the phase shifting deflectometry. The phase shifting deflectometry allows to measure the local slope map and, by the digital derivation, the local curvature variations can be quantified. Deflectometry phase shift is a technique of determining the geometry of a transparent or reflective surface of an object by measuring its slopes and local curvatures from the distortion of the image of a reflected sight or transmitted by the surface of the object.

The use of a such specific technology, based on deflectometry, adapted for an automated inspecting of the fragmentation pattern under ECE R43 for automotive glass or under EN2150 for architectural glazing is surprising since this kind of technology is generally used for application such as inspecting optical properties in order to determine the quality of product for its aesthetic aspect and not to analyse precisely and quantitatively a product such as a tempered glass panel after a fragmentation test in order to check if the glass panel has been correctly tempered since the glass panel has be to safe for the customer and must answer to standards.

According to one embodiment of the present invention, images captured are analyzed by a software. Thus, the present invention provide a method of inspecting a fragmentation pattern of a tempered glass panel, following a fragmentation test capable of directly picking up an image of tested glass and dealing with a software capable of analyzing the number of fragments and another operation in an easy and automated way thereby to carry out a fragmentation test with a good operability and high precision.

Thus, the present invention allows to acquire a recording of the fragmentation pattern after the breakage of the glass and to analyse the results. Furthermore,with the present invention there is no more use of photosensitive paper.

Furthermore, with the present invention the storage area to store images for each fragmentation which have to be kept generally for a period of at least ten years is considerably decreased. Indeed, with an automatic device only a numerical back up is required.

Accordingly to the present invention, the quality of information obtained is improved. Today, the fragmentation tests is manually performed by an operator. Operator trends to always look at the same place, the visual perception could be misled. The operator could also be submitted to tiredness and a subjective appreciation. Thus the reliability could be affected. Indeed, each operator has his own technic while an automatic device is repeatable, reproducible with homogeneity. Concerning the analysis of the results, the automatic device allows to analyse the whole glass surface, what the operator generally cannot perform since this process is time consuming. Thus, all fragments on the whole glass surface can be analysed and stored. This is particularly interesting because from one glass panel tested, results can be used to answer to different standards for example from different countries, and also to follow potential evolution of current standards. Indeed, with the current method based on use of photosensitive paper particularly in automotive application, the only information obtained is what is the lowest or highest density of fragment in a square of 5 cm side and its location, what is the length of the longest fragment and its location, and what is the area of the larger fragment and its location.

Accordingly to the present invention, with an automatic analysis, by having a colored map as a function of the density of fragments in each point could be generated. Such information, could be exchanged in order to check for example the quality of products or for example in order to adapt the condition of tempering.

Thus, according to the present invention, the time needed to perform the fragmentation test and analyse the results is considerably decreased. Today, the operator has to prepare the glass before fragmentation with the photosensitive paper and then sticks plastic foil, then he breaks the glass, he illumines it, he develops the photosensitive paper and finally he analyses the results and encodes it in a numerical file. The current process is time consuming. With an automatic device such as described in the present invention, the operator just have to prepare the glass with a plastic foil and break it according to the standards.

According to the present invention, a reflective surface is needed. The present invention presents particularly an advantage for automotive use like for backlite glazing which generally comprise heating wires and black printed areas.

According to a preferred embodiment of the invention, the concave (or internal) side of a window for automotive application is tested since the heating wires and the black printed areas are not reflective in this side. Thus, it is easier to distinguish it, while with classical technics it is difficult to find the difference between heating wires and fragment boundaries. It is understood that the present invention is also applicable on the convex side of glass panel.

Thus, according to the present invention, the heating wires can be detected, thanks to the software, and removed in order to rebuild the fragments which were crossed by the wires.

Furthermore, during the preparation of the glass to test with a sticking plastic foil, folds are created because of the lack of care. With a classical technology or with the current method, these folds can parasite the detection and the counting of the fragments. With the present invention, the picture is acquired in reflection, therefore the folds which are on the other side of the glass do not appear on the image.

Thus, one aim of the present invention is to provide an improved quality test of fragmentation of tempered glass panel. The glass can be architectural glass or automotive glass. The glass can be curved or flat, black enamel and heating network can be printed on.

This invention is, in a preferred embodiment of the invention, implemented in the framework of the respect of the standards EN12150 for architectural glass and ECE R43 for automotive glass but also for internal quality tests and adjustment of the tempering oven settings. It is understood that the present invention can also be implemented in the framework of the respect of others standards like NFF 31-129, a railway standard for tempered glass.

The invention also relates to an installation for inspecting a fragmentation pattern of a tempered glass panel by deflectometry, following a fragmentation test, comprising:
  a support means for the tempered glass panel,
  a display device for projecting a structured light pattern on the surface of at least one portion of the tempered glass panel,
  an image capture device for capturing an image reflected by the surface of the first portion of the tempered glass panel,
  an image processing device for processing the images to determine the fragmentation pattern.

The advantages of the installation for inspecting a fragmentation pattern of a tempered glass panel by deflectometry, following a fragmentation test are the same as those of the method of inspecting a fragmentation pattern of a tempered glass panel by deflectometry, according to the invention and will not be explained in more detail.

DETAILED DESCRIPTION

The invention will now be further described with reference to the accompanying FIGURE, which is a schematic view showing an example of an installation for inspecting a fragmentation device according to one embodiment of the invention.

The fragment testing installation (1) is a device that carries out a fragmentation test to find particularly the number of fragments at a certain position, the area of the greatest fragment, the length of the longest fragment and different points according to a standards such as ECE R43 for automotive glazings or EN 2150 for architectural glazings. According to an embodiment of the present invention, the impact shock done to a certain portion of the tested glass panel, before projecting fringes and capturing the reflected images is done manually. It is understood that the impact could be automated. The fragmentation testing installation is configured to include a display device 3 projecting a structured light pattern on the surface of at least one portion of the tempered glass panel 2, an image capture device 4 for capturing image reflected by the said surface and an image processing device 5 for receiving the image data of the test glass obtained from the image capture device 4 and performing operations such as, calculating of the number of the fragments and finding the area of the greatest fragment and the length of the longest fragment.

According to one form of embodiment, the display device 3 comprises a fringe pattern alternating pale and dark lines.

According to another form of embodiment of the present invention, the fringe pattern has a first series of substantially parallel fringes extending in a first direction and at a pitch p, and a second series of substantially parallel fringes extending in a second direction substantially perpendicular to the first direction and at a pitch p.

According to one form of embodiment, the display device 3 is made in a material comprising illuminating means which are arranged to illuminate the front face of the display device.

The fringe pattern is thus projected on the surface of at least one portion of the tempered glass panel 2.

In the FIGURE, the fringe pattern is projected on the surface of at least one portion of the curved tempered glass panel 4 for automotive use.

According to the FIGURE, the convex side of the tempered glass panel 2 to be tested under standard ECE R43 has been previously covered with a sticking plastic foil and the concave side is analyzed.

It is understood that the tempered glass panel could be a flat or a curved glass panel. In the case of a curved glass panel, the convex side is preferably covered with a transparent plastic sticking foil in order to keep all the fragments together after the impact. It is understood that concave side could also be covered with a plastic foil. When a flat glass is tested, any of the sides could be covered with a plastic foil.

Then, in one form of embodiment, the glass to be tested is placed on a first support 6, itself positioned on a flat second support 7. According to the FIGURE, the test glass panel is positioned on an identical glass with the convex side down oriented as a first support itself positioned on a table 7. When a flat glass is tested, the said glass could be placed directly on a table or a flat surface without need of a first support. For glass panels with a light curvature, only one support can be used for example a flat support. Indeed, in this case there is not a big difference between the glass in shape and the glass flattened due to the breakage and therefore. Concerning curved glass which is mainly met in automotive, there are different possibilities, either the glass is broken without any support and it flattens either a support with an identical shape is used. This support could be an identical glass. If a support is used, its global position can be contained in a plane which is perpendicular to the plane containing the camera axis and perpendicular to the display device. This support can also be placed on a cradle. That allows to position the glass in order to always have its local surface normal to the plane containing the camera axis and normal to the display device.

According to the invention, it is understood that the display device can be mobile in the first and the second direction of the fringes pattern in order to move an image of the fringe pattern reflected by the surface of the glass panel without moving the object itself into the field of view. In another embodiment of the present invention, the display device projects a structured light pattern, and particularly fringes pattern, in a first and a second direction on the tested glass panel. Then, reflected images from the surface of the tested glass panel are captured are processed.

Then an impact shock is applied to a certain portion thereof with a punch. After the impact, fringes pattern is projected on the surface of at least portion of the tempered glass panel to be tested, thanks to a display device 3 placed overhead the fragmented glass. According to the FIGURE, one display device 3 is placed above the fragmented glass. However, a plurality of display devices can be used or a large display device in order to cover all the surface of the tested glass. The display device 3 could also be mobile between a plurality of positions, the movement between successive positions being designed in order to cover all the size of the glass.

Then, thanks to an image capturing device 4 such as a camera placed also overhead the fragmented glass panel to be tested, reflected images are captured and transmitted to a software to automatically analyze reflected images. An image acquisition of the fragmented glass panel is performed for example with the device from Visuol®.

The camera 4 has a field of view and is arranged so that, in its field of view, it is able to capture an image of the fringe pattern reflected from the surface where fringes pattern from the display device 3 have been projected. It is understood that several cameras can be placed in order to cover all the surface of the tested glass. According to the invention, the camera can be fixed or mobile in the first and the second direction of the fringes pattern in order to cover the whole surface of tested glass panel.

Finally, the image is automatically analyzed with a software and a report is automatically created.

According to the size of the glass, the device is able to acquire several images in order to cover the whole surface of the glass, to stitch the pictures together in order to create an image of the whole glass and to analyze this image.

Once the image acquired, the software processes the image. For example, the operator points out the impact point as well as several points on circumference of the black enamel. From these points, the software creates exclusion areas as the circle centered on the impact point and the band round the edges. The software is also able to determine these exclusion areas without help from the operator.

The next step consists to the identification of the heating wires and the different logos by the software. Another way to perform this operation is that the operator points out each heating wire and surrounds the different logos. Then, the software is able to erase the heating wires and to identify the logos. Once, the wires removed, the fragment boundaries which were crossed by the wires have to be rebuilt. This operation is automatically performed by the software.

After all these operations, the software perform the analysis itself. Once the analysis carried out, the software shows for example the square where it have found the lowest and the highest density of fragments. At this steps, the operator can analyze images and modify them. The same principle is implemented for the longest and the largest fragments. Finally, the picture and the results linked are saved on a central server.

The embodiments of the invention described in the foregoing evidently have no limiting nature. Details and improvements can be made thereto in other variants of embodiment without, however, departing from the scope of the invention.

The invention claimed is:

1. A method of inspecting a fragmentation pattern of a tempered glass panel by deflectometry, following a fragmentation test, the method comprising:
    positioning the tempered glass panel in contact with a support;
    positioning a display device and an image capture device on a same side of the tempered glass panel;
    projecting by the display device a structured light pattern on a surface of at least one portion of the tempered glass panel;
    capturing an image produced by reflecting the structured light pattern off the surface of the at least one portion of the tempered glass panel using the image capture device; and
    processing the captured reflected image produced by reflecting the structured light pattern off the surface of the at least one portion of the tempered glass panel to determine the fragmentation pattern by an image processing device.

2. The method according to claim 1, wherein the tempered glass panel is for automotive use and wherein the fragmentation test in carried out in accordance with ECE R43 standard.

3. The method according to claim 1, wherein the tempered glass panel is for architectural use and wherein the fragmentation test in carried out in accordance with EN12150 standard.

4. The method according to claim 1, wherein the images are processed using phase shifting deflectometry.

5. The method according to claim 1, wherein the structured light pattern represents fringes.

6. The method according to claim 1, wherein sufficient images are captured to determine the fragmentation pattern over an entirety of the tempered glass panel.

7. The method according to claim 1, herein the structured light pattern is projected onto a whole surface of the tempered glass panel.

8. The method according to claim 1, wherein the image capture device is a camera.

9. The method according to claim 8, wherein the camera records a reflection of the pattern generated by the projection of the structured light pattern on at least one portion of the tempered glass panel.

10. The method according to claim 1, wherein the image is a distorted image of the reflection of the structured light pattern on the surface of the at least one portion of the tempered glass panel.

11. The method according to claim 1, wherein the tempered glass is a low light transmission glass.

12. An installation for inspecting a fragmentation pattern of a tempered glass panel by deflectometry, following a fragmentation test, comprising:
   a support for the tempered glass panel;
   a display device to project a structured light pattern on a surface of at least one portion of the tempered glass panel;
   an image capture device arranged on a same side of the tempered glass panel as the display device and arranged to capture an image reflected by the surface of the at least one portion of the tempered glass panel; and
   an image processing device to process the captured reflected image produced by reflecting the structured light pattern off the surface of the at least one portion of the tempered glass panel to determine the fragmentation pattern.

13. An installation according to claim 12, wherein the display device projects a fringe pattern including alternating pale and dark lines.

14. An installation according to claim 13, wherein the fringe pattern has a first series of substantially parallel fringes extending in a first direction and a second series of substantially parallel fringes extending in a second direction substantially perpendicular to the first direction.

15. An installation according to claim 12, wherein the tempered glass panel is a curved or flat glass panel.

* * * * *